United States Patent
Subramanian et al.

(10) Patent No.: US 10,464,008 B2
(45) Date of Patent: Nov. 5, 2019

(54) PROCESS FOR PURIFYING A $CO_2$ STREAM IN ORDER TO AVOID CORROSION BY HYDROCHLORIC ACID

(71) Applicant: SABIC Global Technologies B.V., Bergen op Zoom (NL)

(72) Inventors: Selvakumar Subramanian, Bangalore (IN); Dhaneesh Varappurath Sukumaran, Bangalore (IN); Satish Angadi, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/333,471

(22) PCT Filed: Nov. 16, 2017

(86) PCT No.: PCT/IB2017/057179
§ 371 (c)(1),
(2) Date: Mar. 14, 2019

(87) PCT Pub. No.: WO2018/092065
PCT Pub. Date: May 24, 2018

(65) Prior Publication Data
US 2019/0255478 A1    Aug. 22, 2019

Related U.S. Application Data

(60) Provisional application No. 62/422,745, filed on Nov. 16, 2016.

(51) Int. Cl.
*B01D 53/04* (2006.01)
*B01D 53/26* (2006.01)
(Continued)

(52) U.S. Cl.
CPC .......... *B01D 53/04* (2013.01); *B01D 53/265* (2013.01); *B01D 53/68* (2013.01); *C07C 29/48* (2013.01);
(Continued)

(58) Field of Classification Search
None
See application file for complete search history.

(56) References Cited

U.S. PATENT DOCUMENTS

| 6,224,843 B1 | 5/2001 | Ahmed et al. ............. 423/437.1 |
| 2012/0190906 A1 | 7/2012 | Maglio et al. ................. 585/823 |

(Continued)

FOREIGN PATENT DOCUMENTS

| GB | 2020556 A | 5/1979 |
| WO | WO2013/002908 A2 | 1/2013 |

OTHER PUBLICATIONS

International Search Report and Written Opinion from PCT/IB2017/057179 dated Feb. 9, 2018, 11 pages.

*Primary Examiner* — Anita Nassiri-Motlagh
(74) *Attorney, Agent, or Firm* — Norton Rose Fulbright US LLP

(57) ABSTRACT

A process for purifying a by-product stream comprising primarily CO2 that emanates from a an ethylene glycol plant, where the by-product stream may contain organic chlorides and water. The process employs an adsorbent to remove one or more organic chlorides from the by-product stream to produce pure or substantially pure CO2. To improve the efficiency of the organic chloride adsorbent, prior to the organic chloride adsorption process, a moisture adsorbent may be employed to remove at least some of the water from the by-product stream.

20 Claims, 4 Drawing Sheets

(51) Int. Cl.
  *B01D 53/68*  (2006.01)
  *C07C 29/48*  (2006.01)
  *C07C 31/20*  (2006.01)

(52) U.S. Cl.
  CPC ...... *C07C 31/202* (2013.01); *B01D 2253/108* (2013.01); *B01D 2256/22* (2013.01); *B01D 2257/2064* (2013.01)

(56) References Cited

U.S. PATENT DOCUMENTS

| | | | |
|---|---|---|---|
| 2014/0296607 A1 | 10/2014 | Baptist et al. | 585/822 |
| 2016/0251226 A1 | 9/2016 | Mammadov et al. | 423/437.1 |

PROCESS FOR PURIFYING A CO$_2$ STREAM IN ORDER TO AVOID CORROSION BY HYDROCHLORIC ACID

CROSS REFERENCE TO RELATED APPLICATIONS

This application is a national phase application under 35 U.S.C. § 371 of International Application No. PCT/IB2017/057179 filed Nov. 16, 2017, which claims priority to U.S. Provisional Patent Application No. 62/422,745 filed Nov. 16, 2016. The entire contents of each of the above-referenced disclosures is specifically incorporated by reference herein without disclaimer.

FIELD OF INVENTION

The present invention relates to the purification of carbon dioxide streams produced in petrochemical plants. More specifically, the present invention relates to the purification of carbon dioxide streams having organic chlorides therein.

BACKGROUND OF THE INVENTION

The market for carbon dioxide (CO$_2$) is wide ranging and includes food production, enhanced oil recovery, methanol production etc. One source for carbon dioxide is ethylene glycol plants. The production of ethylene glycol involves the oxidation of ethylene, which can produce CO$_2$ streams as a by-product (off-gas). These CO$_2$ streams, typically, are contaminated with organic chlorides, saturated and unsaturated hydrocarbons, and water.

In contemporary CO$_2$ purification plants having a CO$_2$ feed stream from an ethylene glycol plant, the CO$_2$ feed stream, which contains saturated and un-saturated hydrocarbons along with one or more organic chlorides, undergoes a catalytic oxidation process using a noble metal catalyst in the presence of excess oxygen. The catalytic oxidation process oxidizes organic chloride, which leads to the formation of hydrochloric acid (HCl). Hydrochloric acid is corrosive and causes corrosion of equipment, such as heat exchangers, that are downstream from the catalytic oxidation process that forms the hydrochloric acid.

FIG. 1 provides an illustration of such a prior art system 10. In FIG. 1, CO$_2$ feed stream S100 is fed to multi-stage compressor 100. Multi-stage compressor 100 performs multi-stage compression of CO$_2$ feed stream S100 to form compressed CO$_2$ feed stream S101. This multistage compression of CO$_2$ feed stream S100 removes some of the water from CO$_2$ feed stream S100. The multistage compression of CO$_2$ feed stream S100 also causes compressed CO$_2$ feed stream S101 to have a higher pressure and temperature than CO$_2$ feed stream S100. Compressed feed stream S101 is flowed to heat exchanger 101, which heats compressed CO$_2$ feed stream S101 to form hot CO$_2$ stream S102. Hot CO$_2$ stream S102 is at a temperature and pressure sufficient to facilitate catalytic oxidation of the saturated and unsaturated hydrocarbons and organic chlorides in catalytic oxidation reactor 102. The catalytic oxidation reactions in catalytic oxidation reactor 102 oxidize the saturated and unsaturated hydrocarbons and organic chlorides and thereby form CO$_2$, water (H$_2$O), and HCl. Catalytic output stream S103 of catalytic oxidation reactor 102 is passed through a series of heat exchangers, represented in FIG. 1 as heat exchanger 103, which condenses gaseous HCl and water vapor to form liquid HCl in stream S104. Stream S104 is flowed to HCl absorber 104 where HCl is absorbed. The HCl formed in the catalytic oxidation process causes dew point corrosion in equipment downstream of catalytic oxidation reactor 102, which can result in equipment failure and shutdown of the CO$_2$ purification operation. The equipment that may be most susceptible to HCl corrosion is equipment, such as heat exchanger 103, that is downstream catalytic oxidation reactor 102 but upstream HCl absorber 104. It should be noted, however, that, if HCl absorber 104 is ineffective (e.g., due to malfunction), the equipment downstream of HCl absorber 104 may also be subject to HCl corrosion.

Some prior art methods for addressing the issues of HCl corrosion downstream of a catalytic oxidation reactor involve upgrading the metallurgy of heat exchangers downstream of the catalytic oxidation reactor where the dew point corrosion is at its highest level. However, this is an expensive practice.

Another prior art method for addressing the issue of HCl corrosion of equipment involves atomizing NH$_3$/amines in a process stream so that the NH$_3$/amines neutralizes the HCl formed at the dew point in the catalytic output stream. However, for this method, the equipment requires regular washing with water to remove salts formed from the neutralization reaction. Additionally, this method requires an accumulator to remove the amines and the wash water.

BRIEF SUMMARY OF THE INVENTION

A discovery has been made that provides a solution to the aforementioned issues regarding purification of CO$_2$ by-product gas stream from an ethylene glycol plant to produce substantially pure CO$_2$. The discovered process is premised on removing one or more compounds that react to form HCl from the CO$_2$ by-product gas stream prior to the CO$_2$ by-product gas stream entering as feed into a catalytic reactor. In this way, the issue of HCl corrosion is addressed by preventing, or reducing, the formation of HCl, instead of attempting to mitigate HCl's effect once it is formed.

The CO$_2$ by-product gas stream may contain trace amounts of organic chlorides and water. The CO$_2$ by-product gas stream may also contain unsaturated and saturated hydrocarbons. The discovered process uses an adsorbent to remove one or more organic chlorides from the CO$_2$ by-product gas stream because these organic chlorides can oxidize to form HCl. In embodiments of the discovered process, a sodium form of zeolite-13X having Si:Al ratio of 1.5:1 to 2.5:1, preferably 2:1 or thereabout, under set conditions of pressure, temperature, and space velocity is used to adsorb the one or more organic chlorides from the CO$_2$ by-product gas stream. In embodiments of the discovered process, a moisture adsorbent is used to remove at least some of the water from the CO$_2$ stream, prior to the organic chloride adsorption process, in order to improve the efficiency of the organic chloride adsorbent process.

By implementing embodiments of the invention, the expense of designing and/or installing equipment to withstand HCl corrosion, maintaining HCl absorbers, and the operational difficulties of removing salts amines and water, associated with prior art methods discussed above may be avoided. Alternatively, embodiments of the invention may be implemented with one or more of the prior art methods to have a more robust system to address the corrosive effect of HCl.

Embodiments of the invention include a process for purifying CO$_2$ feed stream comprising primarily CO$_2$, one or more organic chlorides, and water. The process may include cooling the CO$_2$ feed stream to condense and remove at least a portion of the water from the $CO_2$ feed stream to produce a cooled $CO_2$ feed stream that includes less than 0.3 wt. % water. The process may further include contacting the cooled $CO_2$ feed stream with a zeolite adsorbent material to remove at least a portion of the organic chloride(s) from the cooled $CO_2$ feed stream to produce a purified $CO_2$ feed stream.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, twenty embodiments are now described. Embodiment 1 is a process for purifying a carbon dioxide ($CO_2$) feed stream containing primarily $CO_2$, an organic chloride(s), and water, the process including the steps of cooling the $CO_2$ feed stream to condense and remove at least a portion of the water from the $CO_2$ feed stream to produce a cooled $CO_2$ feed stream comprising less than 0.3 wt. % water; and contacting the cooled $CO_2$ feed stream with a zeolite adsorbent material to remove at least a portion of the organic chloride(s) from the cooled $CO_2$ feed stream to produce a purified $CO_2$ feed stream. Embodiment 2 is the process of embodiment 1 further including, prior to contacting the cooled $CO_2$ feed stream with a zeolite adsorbent material, contacting the cooled $CO_2$ feed stream with a silica adsorbent material to remove additional water, if present, from the cooled $CO_2$ feed stream. Embodiment 3 is the process of any of embodiments 1 and 2, wherein the $CO_2$ feed stream comprises 5 to 600 ppm of an organic chloride(s). Embodiment 4 is the process of any of embodiments 1 to 3, wherein the cooling of the $CO_2$ feed stream contains cooling the $CO_2$ feed stream to a temperature of 35° C. to 55° C. Embodiment 5 is the process of embodiment 4 further including the step of cooling the cooled $CO_2$ feed stream to a temperature of 10° C. to 30° C. to condense and remove additional water, if present, from the cooled $CO_2$ feed stream such that it contains less than 0.06 wt. % water. Embodiment 6 is the process of any of embodiments 1 to 5, wherein the zeolite adsorbent material contains zeolite-13X having a Si/Al ratio of 2 or less. Embodiment 7 is the process of any of embodiments 1 to 5, wherein the zeolite adsorbent material contains zeolite-13X adsorbent material having Si:Al ratio in the range of 1.5:1 to 2.5:1. Embodiment 8 is the process of any of embodiments 1 to 7, wherein the $CO_2$ feed stream is from an ethylene glycol plant. Embodiment 9 is the process of any of embodiments 1 to 8, wherein the purified $CO_2$ feed stream is used as a reactant for an oxidation reaction. Embodiment 10 is the process of embodiment 9, wherein the amount of hydrochloric acid (HCl) produced in the oxidation reaction is 0 to <0.02 ppmv. Embodiment 11 is the process of any of embodiments 1 to 10, wherein the organic chloride(s) contain ethylene di-chloride. Embodiment 12 is the process of any of embodiments 1 to 11, wherein the $CO_2$ feed stream contains 99 to 99.5 vol. %. Embodiment 13 is the process of any of embodiments 1 to 12, wherein the $CO_2$ feed stream contains 5 to 100 ppmv organic chloride(s). Embodiment 14 is the process of any of embodiments 1 to 13, wherein the adsorption conditions include a temperature of 15 to 50° C. Embodiment 15 is the process of any of embodiments 1 to 14, wherein the adsorption conditions include a pressure of 15 to 25 barg. Embodiment 16 is the process of any of embodiments 1 to 15, wherein the adsorption conditions include a space velocity of 1 to 5 hl. Embodiment 17 is the process of any of embodiments 1 to 16, wherein the cooling the $CO_2$ feed stream includes cooling by a cooling water heat exchanger. Embodiment 18 is the process of any of embodiments 1 to 17, wherein the cooling the $CO_2$ feed stream includes cooling by a chiller unit. Embodiment 19 is the process of and of embodiments 1 to 18, wherein the $CO_2$ feed stream, prior to purification, further contains saturated and unsaturated hydrocarbons. Embodiment 20 is the process of any of embodiments 1 to 19, wherein an HCl absorber is not used.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE DISCLOSURE

A discovery has been made for purifying a by-product stream comprising primarily $CO_2$ from an ethylene glycol producing plant. The by-product stream may also contain organic chlorides and water. According to embodiments of the invention, an adsorbent is employed to remove one or more organic chlorides from the $CO_2$ by-product stream prior to catalytic oxidation to produce pure or substantially pure $CO_2$. In embodiments of the invention, a moisture adsorbent is used to remove at least some of the water from the $CO_2$ stream, prior to the organic chloride adsorption process, in order to improve the efficiency of the organic chloride adsorbent process.

By removing one or more organic chlorides from the $CO_2$ by-product stream, one or more compounds that react to form HCl is removed from the feed to a catalytic oxidation reactor employed in the purification of the $CO_2$ by-product stream, thereby preventing, or at least reducing, the formation of HCl in the catalytic oxidation reactor. In this way, the issue of HCl corrosion of equipment downstream from the catalytic oxidation reactor is addressed by preventing, or reducing, the formation of HCl, instead of attempting to mitigate HCl's effect once it is formed.

Embodiments of the invention includes a process that uses zeolite-13X (Si:Al ratio of 1.5:1 to 2.5:1, preferably 2:1 or thereabout) to remove the organic chlorides, in particular ethylene dichloride (EDC), from the impure $CO_2$ by-product gas of the ethylene glycol plant. However, it is contemplated that other zeolites can be used to remove organic chlorides from the $CO_2$ stream. Non-limiting examples of other zeolites that can be used in the context of the present invention include zeolite-Y, zeolite-X, ZSM-5, etc.

Figure 1:
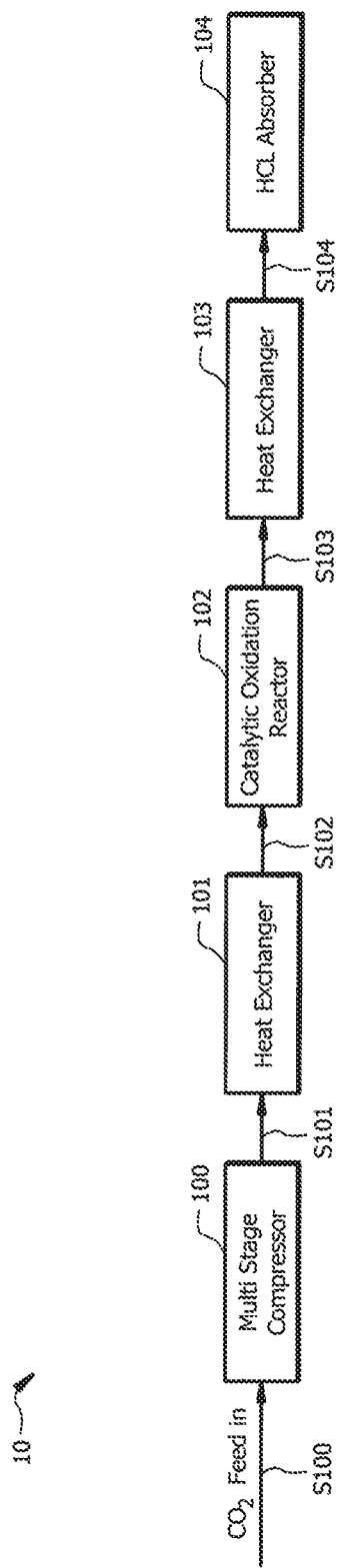
FIG. 1 shows a prior art system for purifying a $CO_2$ stream from an ethylene glycol plant.
Figure 2:
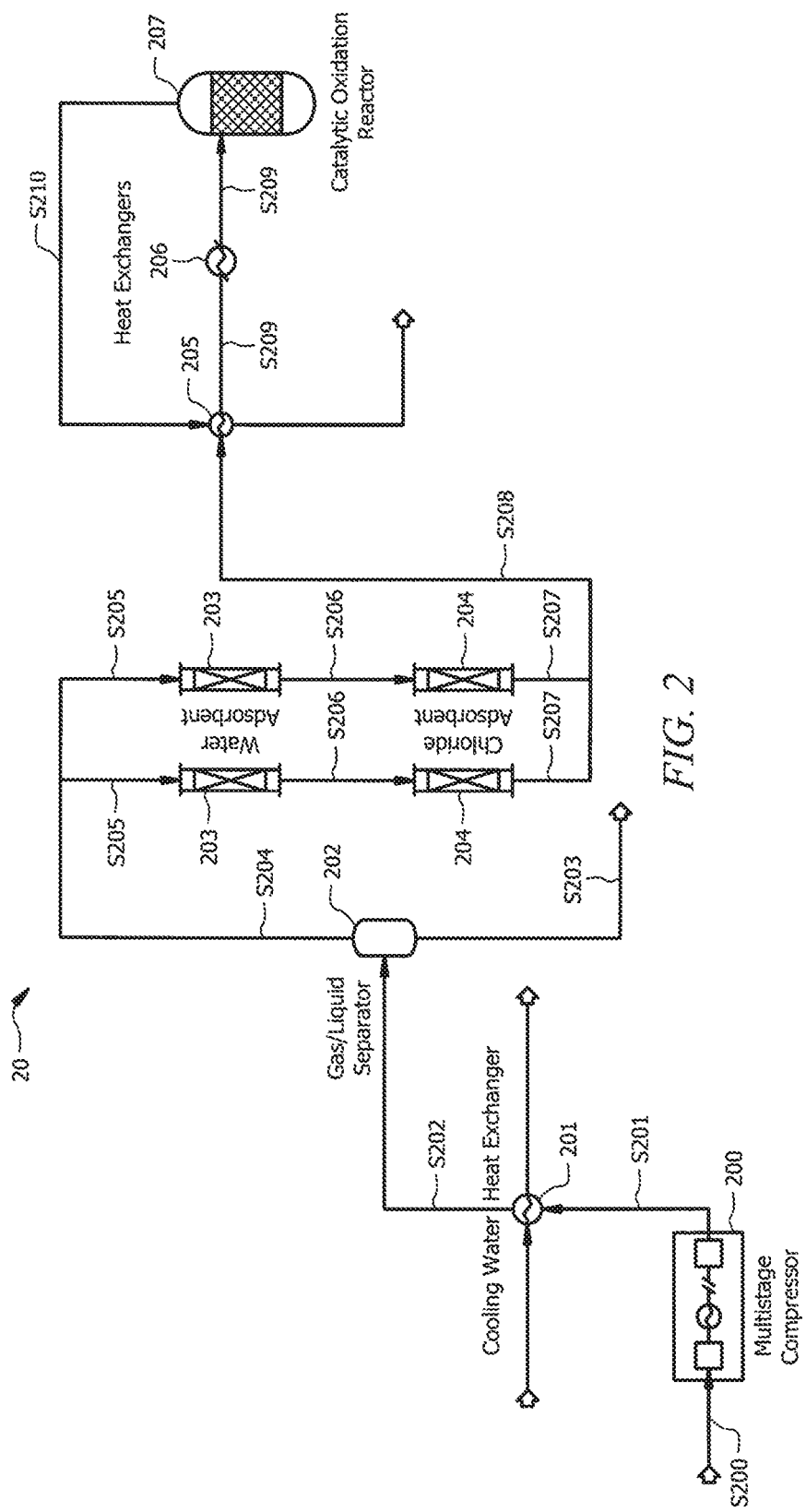
FIG. 2 shows a system for purifying a $CO_2$ stream from an ethylene glycol plant, according to embodiments of the invention.

Referring to FIG. 2, system 20 for purifying a $CO_2$ stream from an ethylene glycol plant is shown. $CO_2$ feed stream S200 may include 99.5 Vol % $CO_2$, approximately 5-100 ppmv organic chloride (e.g., ethylene dichloride ($C_2H_4Cl_2$)), approximately 1 ppmv unsaturated hydrocarbons, and approximately 1 ppmv saturated hydrocarbons. $CO_2$ feed stream S200 is fed to multi-stage compressor 200. Multi-stage compressor 200 performs multi-stage compression of $CO_2$ feed stream S200 to form compressed $CO_2$ feed stream S201. This multistage compression of $CO_2$ feed stream S200 removes at least some of the water from $CO_2$ feed stream S200 such that compressed $CO_2$ feed stream S201 has a lower water content than $CO_2$ feed stream S200. The multistage compression of $CO_2$ feed stream S200 also causes compressed $CO_2$ feed stream S201 to have a higher pressure and temperature than $CO_2$ feed stream S200. Compressed $CO_2$ feed stream S201 is flowed to heat exchanger 201, which cools compressed $CO_2$ feed stream S201 to form cooled $CO_2$ stream S202 at a temperature in the range of 35 to 55° C., and all ranges and values there between including ranges 35° C. to 40° C., 40° C. to 45° C., 45° C. to 50° C., 50° C. to 55° C. and values 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., and 55° C., preferably a temperature 45° C. or thereabout. At this temperature, $H_2O$ vapor from compressed feed stream S201 condenses to liquid $H_2O$ in cooled stream S202. Heat exchanger 201 may use water as the cooling fluid. However, in embodiments of the invention, other cooling fluids may be used.

Cooled stream S202 may be routed to gas/liquid separator 202 to have the liquid $H_2O$ removed from cooled $CO_2$ stream S202. Specifically, gas/liquid separator 202 separates cooled $CO_2$ stream S202 into liquid stream S203 and $CO_2$ vapor stream S204. $CO_2$ vapor stream S204, emerging from gas/liquid separator 202, may have water content in the range of 0.1 to 0.6 wt. %, and all ranges and values there between including ranges 0.1 to 0.2 wt. %, 0.2 to 0.3 wt. %, 0.3 to 0.4 wt. %, 0.4 to 0.5 wt. %, 0.5 to 0.6 wt. % and values 0.1 wt. %, 0.2 wt. %, 0.3 wt. %, 0.4 wt. %, 0.5 wt. %, and 0.6 wt. %, preferably 0.2 wt. % or thereabout or less than 0.3 wt. %. From gas/liquid separator 202, $CO_2$ vapor stream S204 may be split into two $CO_2$ vapor streams S205, where each vapor stream S205 may be flowed to one of water adsorbent beds 203. Water adsorbent beds 203 may include silica/molecular sieve adsorbent material, non-limiting examples of which include silica gel, activated carbon, and its composite materials, faujasite zeolite, zeolite type 3A etc. In FIG. 2, two adsorbent beds are shown but any number of adsorbent beds may be used in the context of the present invention (e.g., 3, 4, 5, 6, 7, or more adsorbent beds). Water adsorbent beds 203 are adapted to remove water present in $CO_2$ vapor streams S205 to form dry $CO_2$ vapor streams S206, which have no water or a small amount of water in them (e.g., 0 wt. % to 0.2 wt. % of water).

Dry $CO_2$ vapor streams S206 are flowed to organic chloride adsorbent beds 204. Organic chloride adsorbent beds 204 may include zeolite-13X adsorbent material (Si:Al ratio of 1.5:1 to 2.5:1, preferably 2:1 or thereabout or less than 2:1). Organic chloride adsorbent beds 204 are adapted to remove organic chlorides from dry $CO_2$ vapor streams S206 to form purified $CO_2$ vapor streams S207. In embodiments of the invention, organic chloride adsorbent beds 204 cause the adsorption of organic chloride at a pressure of 15 to 25 barg, temperature of 15 to 50° C., and space velocity of 1 to 5 $hr^{-1}$. Purified $CO_2$ vapor streams S207 may be combined to form purified $CO_2$ vapor stream S208. Purified $CO_2$ vapor stream S208 may be heated in heat exchanger 205 and heat exchanger 206 to form hot purified $CO_2$ vapor stream S209. The heating fluid in heat exchanger 205 may be product stream S210 from catalytic oxidation reactor 207. In embodiments of the invention, other fluids may be used as heating fluid.

After heating in heat exchanger 205 and heat exchanger 206, hot purified $CO_2$ vapor stream S209 is sent to catalytic oxidation reactor 207. Because there is no organic chloride (or reduced amounts of organic chloride, e.g., a maximum of 0.01 ppmv in $CO_2$ vapor stream 209 (as compared to $CO_2$ feed stream S200), formation of HCl is prevented (or substantially reduced) during the catalytic oxidation process that takes place in catalytic oxidation reactor 207. In embodiments of the invention, during the catalytic oxidation process, no HCl is produced or, if any HCl is produced, the quantity is so small that it is non-detectable. In embodiments of the invention, the maximum amount of HCl produced in and flows from catalytic oxidation reactor 207 is <0.02 ppmv. In this way, HCl, the main cause for corrosion in the downstream heat exchanger is avoided.

Figure 3:
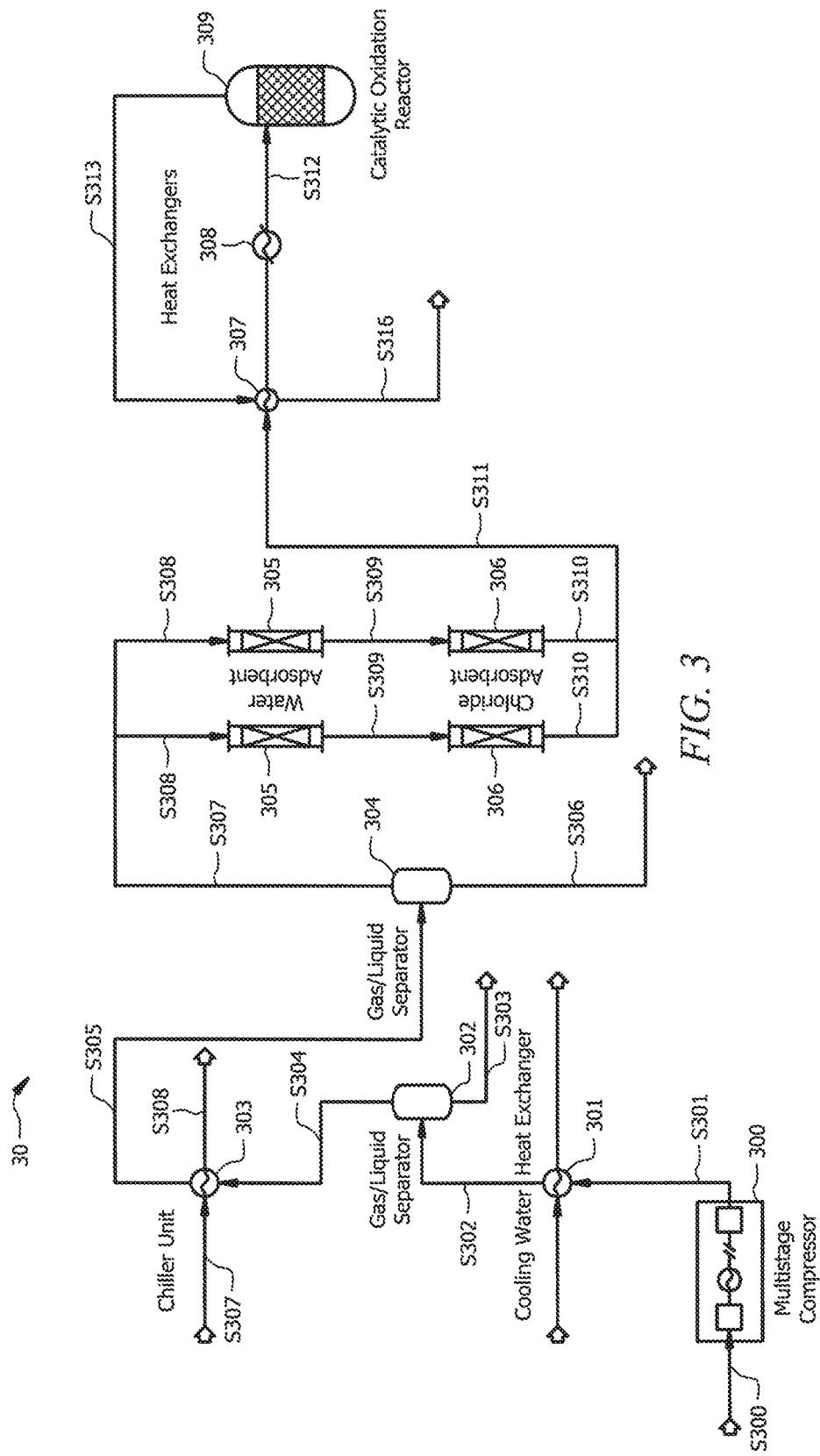
FIG. 3 shows a system for purifying a $CO_2$ stream from an ethylene glycol plant, according to embodiments of the invention.

Another non-limiting embodiment of the present invention is provided in FIG. 3. Referring to FIG. 3, system 30 for purifying a $CO_2$ stream from an ethylene glycol plant is shown. $CO_2$ feed stream S300 may include 99.5 vol. % $CO_2$, approximately 5-100 ppmv organic chloride (e.g., ethylene dichloride ($C_2H_4Cl_2$)), approximately 1 ppmv unsaturated hydrocarbons, and approximately 1 ppmv saturated hydrocarbons. $CO_2$ feed stream S300 is fed to multi-stage compressor 300. Multi-stage compressor 300 performs multi-stage compression of $CO_2$ feed stream S300 to form compressed $CO_2$ feed stream S301. This multistage compression of $CO_2$ feed stream S300 removes at least some of the water from $CO_2$ feed stream S300 such that compressed $CO_2$ feed stream S301 has a lower water content than $CO_2$ feed stream S300. The multistage compression of $CO_2$ feed stream S300 also causes compressed $CO_2$ feed stream S301 to have a higher pressure and temperature than $CO_2$ feed stream S300. Compressed $CO_2$ feed stream S301 is flowed to heat exchanger 301, which cools compressed $CO_2$ feed stream S301 to form cooled $CO_2$ stream S302 at a temperature in the range of 35 to 55° C., and all ranges and values there between including ranges 35° C. to 40° C., 40° C. to 45° C., 45° C. to 50° C., 50° C. to 55° C. and values 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., and 55° C., preferably a temperature of 45° C. or thereabout. At this temperature, $H_2O$ vapor from compressed feed stream S301 condenses to liquid $H_2O$ in cooled stream S302. Heat exchanger 301 may use water as the cooling fluid. However, in embodiments of the invention, other cooling fluids may be used.

Cooled stream S302 may be routed to gas/liquid separator 302 to have the condensed $H_2O$ removed from cooled $CO_2$ stream S302. Specifically, gas/liquid separator 302 separates cooled $CO_2$ stream S302 into liquid stream S303 and $CO_2$ vapor stream S304. $CO_2$ vapor stream S304, emerging from gas/liquid separator 302, may have water content in the range of 0.1 to 0.6 wt. %, and all ranges and values there between including ranges 0.1 to 0.2 wt. %, 0.2 to 0.3 wt. %, 0.3 to 0.4 wt. %, 0.4 to 0.5 wt. %, 0.5 to 0.6 wt. % and values 0.1 wt. %, 0.2 wt. %, 0.3 wt. %, 0.4 wt. %, 0.5 wt. %, and 0.6 wt. %, preferably 0.2 wt. % or thereabout or less than 0.3 wt. %.

From gas/liquid separator 302, $CO_2$ vapor stream S304 may be routed to chiller unit 303. Chiller unit 303 may cool $CO_2$ vapor stream S304 to form chilled $CO_2$ vapor stream S305 at a temperature in the range of 10° C. to 30° C., and all ranges and values there between including ranges 10° C. to 15° C., 15° C. to 20° C., 20° C. to 25° C., 25° C. to 30° C. and values 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., and 30° C., preferably 20° C. or thereabout. Chilled $CO_2$ vapor stream S305 may be then routed to gas/liquid separator 304, which removes Liquid $H_2O$ from chilled $CO_2$ vapor stream S305 to form liquid stream S306 and $CO_2$ vapor stream S307. $CO_2$ vapor stream S307 may have a temperature in the range of 10 to 30° C., and all ranges and values there between including ranges 10° C. to 15° C., 15° C. to 20° C., 20° C. to 25° C., 25° C. to 30° C. and values 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., and 30° C., preferably 20° C. or thereabout, and water content in the range of 0.01 to 0.1 wt. %, and all ranges and values there between including 0.01 wt. %, 0.02 wt. %, 0.03 wt. %, 0.04 wt. %, 0.05 wt. %, 0.06 wt. %, 0.07 wt. %, 0.08 wt. %, 0.09 wt. %, and 0.1 wt. %, preferably 0.05 wt. % or thereabout or less than 0.06 wt. %. $CO_2$ vapor stream S307 may also include organic chloride such as ethylene dichloride.

$CO_2$ vapor stream S307 may be split into two $CO_2$ vapor streams S308, where each stream S308 is flowed to one of water adsorbent beds 305. In FIG. 3, two adsorbent beds are shown but any number of adsorbent beds may be used in the context of the present invention (e.g., 3, 4, 5, 6, 7, or more adsorbent beds). Water adsorbent beds 305 may include silica/molecular sieve adsorbent material, non-limiting examples of which include silica gel, activated carbon, and its composite materials, faujasite zeolite, zeolite type 3A etc. Water adsorbent beds 305 are adapted to remove water present in $CO_2$ vapor streams S307 to form dry $CO_2$ vapor streams S309, which have no water or a small amount of water in them (e.g., 0 wt. % to 0.001 wt. % of water).

Dry $CO_2$ vapor streams S309 are flowed to organic chloride adsorbent beds S306. Organic chloride adsorbent beds 306 may include zeolite-13X adsorbent material (Si:Al ratio of 1.5:1 to 2.5:1, preferably 2:1 or thereabout or less than 2:1). However, it is contemplated that other zeolites can be used to remove organic chlorides from the $CO_2$ stream. Non-limiting examples of other zeolites that can be used in the context of the present invention include Zeolite-Y, Zeolite-X, ZSM-5 etc. Organic chloride adsorbent beds 306 are adapted to remove organic chlorides from dry $CO_2$ vapor streams S309 to form purified $CO_2$ vapor streams S310. In embodiments of the invention, organic chloride adsorbent beds 306 results in the adsorption of organic chloride at a pressure of 15 to 25 barg, temperature of 10 to 50° C., and space velocity is 1-5 $hr^1$. Purified $CO_2$ vapor streams S310 may be combined to form purified $CO_2$ vapor stream S311. Purified $CO_2$ vapor stream S311 may be heated in heat exchanger 307 and heat exchanger 308 to form hot purified $CO_2$ vapor stream S311. The heating fluid in heat exchanger 307 may be product stream S313 from catalytic oxidation reactor 309. In embodiments of the invention, other fluids may be used as heating fluid.

After heating in heat exchanger 307 and heat exchanger 308, hot purified $CO_2$ vapor stream S312 is sent to catalytic oxidation reactor 309. Because there is no organic chloride (or reduced amounts of organic chlorides (e.g., a maximum of 0.01 ppmv) in $CO_2$ stream 312 (as compared to $CO_2$ feed stream S300), formation of HCl is prevented (or substantially prevented) during the catalytic oxidation process that takes place in catalytic oxidation reactor 309. In embodiments of the invention, during the catalytic oxidation process, no HCl is produced or, if any HCl is produced, the quantity is so small that it is non-detectable. In embodiments of the invention, the maximum amount of HCl produced in and flows from catalytic oxidation reactor 309 is <0.02 ppmv. In this way, HCl, the main cause for corrosion in the downstream heat exchanger is avoided.

By implementing either of system 20 or system 30 in a $CO_2$ purification plant, any one or all of the following benefits can be achieved: (1) the expense of designing and installing equipment to withstand HCl corrosion can be reduced or avoided; (2) the expense of designing, installing, and maintaining HCl absorbers can be reduced or avoided; and/or (3) the operational difficulties of removing salts amines and water can be reduced or avoided. Alternatively, system 20 or system 30 may be implemented with one or more of the prior art methods to have a more robust system to address the corrosive effect of HCl.

EXAMPLES

Example 1

Adsorption of EDC with Zeolite-13X

Figure 4:
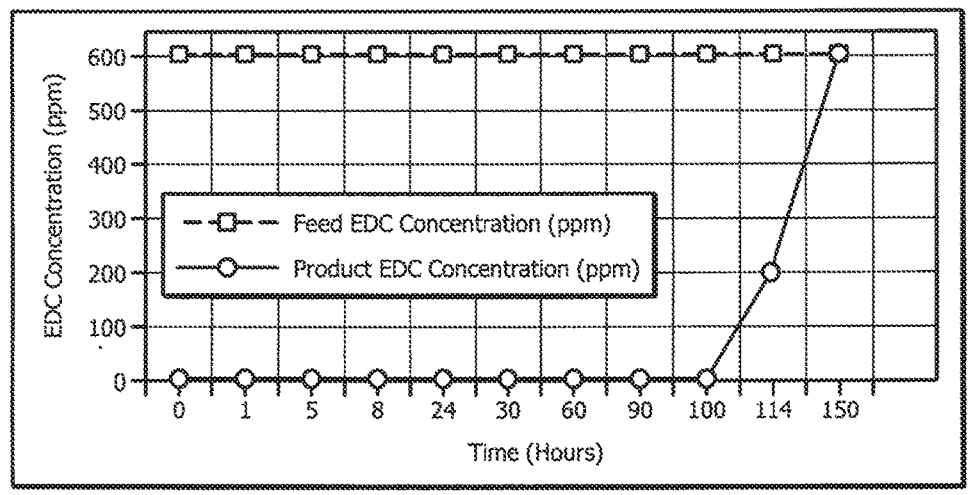
FIG. 4 shows results of an experiment that tested the adsorption properties of zeolite-13X with respect to an organic chloride.

A first adsorption experiment was performed with zeolite-13X at 1 bar pressure and ambient temperature. In this first experiment, 10 grams of zeolite-13X having a diameter of 1.5 mm and length approximately 2 mm was packed in an adsorbent bed reactor and allowed to contact with 10 g/hr of $CO_2$ containing approximately 600 ppm of ethylene dichloride (EDC). The EDC content of the $CO_2$ gas coming out of the adsorbent bed was constantly monitored by gas chromatography (GC). For up to 100 hours of operation, it was observed that there was no EDC coming out of the adsorbent bed. This indicates that zeolite-13X completely adsorbed the EDC during this period of time. FIG. 4 shows results (a plot showing the breakthrough curve) for the first adsorption experiment.

Example 2

Adsorption of EDC with Zeolite-13X in Presence of Water

Figure 5:
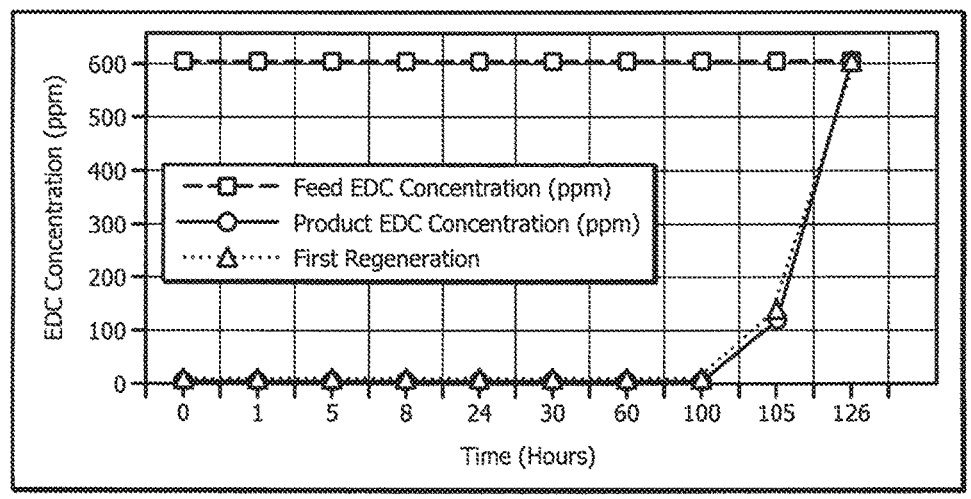
FIG. 5 shows results of experiments that tested the adsorption properties of zeolite-13X with respect to an organic chloride in the presence of water.

A second adsorption experiment was performed. This experiment was performed with zeolite-13X in the presence of water vapor. In this second experiment, 20 grams of zeolite-13X having a diameter of 1.5 mm and length approximately 2 mm was packed in an adsorbent bed reactor and allowed to contact with 10 g/h of $CO_2$ containing approximately 600 ppm of EDC and approximately 200 ppm of water vapor. An approximately 30% reduction in EDC adsorption capacity of zeolite-13X was observed for this second experiment as compared to the first experiment that did not have water in the inlet feed. FIG. 5 shows results (a plot showing the breakthrough curve) for the second adsorption experiment. The reduction in adsorption capacity of zeolite-13X in the second experiment may be due the competitive adsorption of water at the same sites where EDC gets adsorbed. In the second experiment, the time taken to get the breakthrough is 96 hrs. Based on these experimental results, it is observed that the adsorption capacity of zeolite-13X has been reduced from 6 wt. % to 4 wt. % because of the presence of water.

Example 3

Adsorption of EDC with Regenerated Zeolite-13X in Presence of Water

A third experiment was conducted. This experiment was conducted with regenerated catalyst at the same operating condition mentioned for 600 ppm of EDC and approximately 200 ppm of water vapor). The regeneration was carried out at 250° C. under the $N_2$ flow of 120 ml/min for 4 hrs. The results of this experiment are shown in FIG. 5. FIG. 5 shows that the adsorption property of regenerated catalyst is very similar to that of fresh adsorbent. From these experimental results, it is clear that zeolite-13X can be used for repeated adsorption experiments.

Based on the results from Examples 1 to 3, it may be concluded that zeolite-13X may be used effectively in the adsorption of organic chloride in $CO_2$ streams. Further, the results show that regenerated zeolite-13X is also effective, which is a significant factor in designing cost effective removal systems.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

The invention claimed is:

1. A process for purifying a carbon dioxide ($CO_2$) feed stream comprising primarily $CO_2$, an organic chloride, and water, the process comprising:
    cooling the $CO_2$ feed stream to condense and remove at least a portion of the water from the $CO_2$ feed stream to produce a cooled $CO_2$ feed stream comprising less than 0.3 wt. % water; and
    contacting the cooled $CO_2$ feed stream with a zeolite adsorbent material to remove at least a portion of the organic chloride from the cooled $CO_2$ feed stream to produce a purified $CO_2$ feed stream.

2. The process of claim 1 further comprising:
    prior to contacting the cooled $CO_2$ feed stream with a zeolite adsorbent material, contacting the cooled $CO_2$ feed stream with a silica adsorbent material to remove additional water from the cooled $CO_2$ feed stream.

3. The process of claim 1, wherein the $CO_2$ feed stream comprises 5 to 600 ppm of an organic chloride.

4. The process of claim 1, wherein the cooling of the $CO_2$ feed stream comprises cooling the $CO_2$ feed stream to a temperature of 35° C. to 55° C.

5. The process of claim 4 further comprising:
    cooling the cooled $CO_2$ feed stream to a temperature of 10° C. to 30° C. to condense and remove additional water, if present, from the cooled $CO_2$ feed stream such that it comprises less than 0.06 wt. % water.

6. The process of claim 1, wherein the zeolite adsorbent material comprises zeolite-13X having a Si/Al ratio of 2 or less.

7. The process of claim 1, wherein the zeolite adsorbent material comprises zeolite-13X adsorbent material having Si:Al ratio in the range of 1.5:1 to 2.5:1.

8. The process of claim 1, wherein the $CO_2$ feed stream is from an ethylene glycol plant.

9. The process of claim 1, wherein the purified $CO_2$ feed stream is used as a reactant for an oxidation reaction.

10. The process of claim 9, wherein the amount of hydrochloric acid (HCl) produced in the oxidation reaction is 0 to <0.02 ppmv.

11. The process of claim 1, wherein the organic chloride comprises ethylene di-chloride.

12. The process of claim 1 wherein the $CO_2$ feed stream comprises 99 to 99.5 vol. % $CO_2$.

13. The process of claim 1, wherein the $CO_2$ feed stream comprises 5 to 100 ppmv organic chloride.

14. The process of claim 1, wherein the adsorption conditions comprise a temperature of 15 to 50° C.

15. The process of claim 1, wherein the adsorption conditions comprise a pressure of 15 to 25 barg.

16. The process of claim 1, wherein the adsorption conditions comprise a space velocity of 1 to 5 $h^1$.

17. The process of claim 1 wherein the cooling of the $CO_2$ feed stream comprises cooling by a cooling water heat exchanger.

18. The process of claim 1 wherein the cooling of the $CO_2$ feed stream comprises cooling by a chiller unit.

19. The process of claim 1, wherein the $CO_2$ feed stream, prior to purification, further comprises saturated and unsaturated hydrocarbons.

20. The process of claim 1, wherein an HCl absorber is not used.

* * * * *